(12) United States Patent
Galati

(10) Patent No.: US 8,246,420 B1
(45) Date of Patent: Aug. 21, 2012

(54) PORTABLE DEBRIS CONTAINER UNIT FOR SANDING/MICRO-ETCHING PROCESSES ON DENTAL ELEMENTS

(76) Inventor: James R. Galati, Scottsdale, AZ (US)

( * ) Notice: Subject to any disclaimer, the term of this patent is extended or adjusted under 35 U.S.C. 154(b) by 1045 days.

(21) Appl. No.: 12/228,126

(22) Filed: Aug. 11, 2008

(51) Int. Cl.
*B24C 9/00* (2006.01)

(52) U.S. Cl. ............... 451/89; 134/200; 312/1; 451/451

(58) Field of Classification Search .................. 134/200; 232/31; 312/1, 31.2; 451/89, 90, 451
See application file for complete search history.

(56) References Cited

U.S. PATENT DOCUMENTS

| | | | | |
|---|---|---|---|---|
| 4,059,903 A | * | 11/1977 | Piet et al. ........................... | 312/1 |
| 4,268,392 A | | 5/1981 | Hayes | |
| 4,993,199 A | * | 2/1991 | Hughes ............................ | 451/88 |
| 5,095,925 A | * | 3/1992 | Elledge et al. ................... | 134/61 |
| 5,177,911 A | * | 1/1993 | Ruemelin et al. ................ | 451/89 |
| 5,295,333 A | * | 3/1994 | Puschner ....................... | 451/100 |
| 5,531,722 A | | 7/1996 | Van Hale | |
| 5,971,837 A | * | 10/1999 | McDavid ......................... | 451/89 |
| 6,133,339 A | | 10/2000 | Xie et al. | |
| 6,364,748 B1 | * | 4/2002 | Zwicker et al. .................. | 451/38 |
| 6,585,512 B2 | | 7/2003 | Van Hale | |
| 6,592,026 B2 | * | 7/2003 | Vilardi ............................ | 232/17 |
| 7,059,850 B1 | | 6/2006 | Phan et al. | |
| 2002/0182988 A1 | * | 12/2002 | Williams et al. ................ | 451/89 |

* cited by examiner

*Primary Examiner* — Timothy V Eley
(74) *Attorney, Agent, or Firm* — Richard L. Mikesell

(57) ABSTRACT

The problem of controlling dust during an operation such as a micro-etching process, associated with a dental appliance in an efficient and economical manner is solved by a unit which is portable and which encloses the appliance during the micro-etching process.

2 Claims, 3 Drawing Sheets

PORTABLE DEBRIS CONTAINER UNIT FOR SANDING/MICRO-ETCHING PROCESSES ON DENTAL ELEMENTS

TECHNICAL FIELD OF THE INVENTION

The present invention is related generally to the field of dentistry. More particularly, the present invention is related to improved systems and methods associated with the cleaning dental appliances, particularly in the field of orthodontics.

BACKGROUND OF THE INVENTION

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. The brackets and bands are bonded to the patient's teeth using a suitable material, such as dental adhesive. Once the adhesive has set, the archwire is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

After the archwire is in place, periodic meetings with the orthodontist are required, during which the patient's braces will be adjusted. This involves installing different archwires having different force-inducing properties or by replacing or tightening existing ligatures. Between meetings, the patient may be required to wear supplementary appliances, such as elastic bands or headgear, to supply additional or extraoral forces.

Generally the orthodontic archwires are made from a stainless steel wire (spring wire) having a diameter of 0.01 to 0.022 inches for the round wires and cross-section of $0.10 \times 0.020$ to $0.022 \times 0.028$ inches for the rectangular wires. The archwires are constructed of various cross-sectional shapes and designs for applying the desired biasing forces to the teeth. Archwires are frequently referred to as orthodontic appliances. Many archwires of various diameters and configurations are necessary to accomplish the desired positioning of the malaligned or malocclused teeth.

Dental cements are used for adhering dental wires to a patient's teeth during orthodonics as well as for restoratives such as crowns, bridges, inlays and onlays to a tooth, providing a lining in a tooth cavity, fixing orthodontic appliances to the teeth and sealing root canals after endodontic treatment.

The dental profession has traditionally used durable cements for permanent restorations and temporary cements for temporary or provisional restorations. A durable cement is used for permanent restorations and is required to last for at least one year. A temporary cement can be used for up to three months as temporary or up to one year as provisional. The commonly used dental cements for long term restorations are zinc phosphate cement, zinc poly(carboxylate) cement, glass ionomer cement and composite cement.

It has been discovered that orthodontic brackets and similar devices can be adhesively bonded directly to a tooth surface and held in any desired position on the tooth without the necessity of clamps and the like, and the same become securely adhered to the tooth within a matter of a few minutes. This is of substantial advantage to the orthodontist and to the patient as it permits the attachment of the brackets and the arch-wires in the same sitting. The manner of attachment by which this is accomplished is to adhere the orthodontic bracket or other such device to a prepared tooth surface by using a catalyzed thixotropic acrylic or methacrylic ester monomer mix.

However, if the appliance, such as a bracket, a crown, must be modified in some manner, the adhesive must be removed. This is often done by micro-etching. Micro-etching may generate "sand" and debris which must be controlled. In some instances, large units are required to ensure the control of such materials. This is not desirable, but is especially problematic for a doctor who has several satellite offices as the cost may become prohibitive to have such a unit in each office.

Therefore, there is a need for a portable means to control "sand" or other such debris during a micro-etching process on a dental accessory such as a bracket or a crown.

SUMMARY OF THE INVENTION

These, and other, objects are achieved by a portable unit that traps and contains the "sand" and debris generated from a micro-etcher being used to remove cement or the like from dental appliances such as orthodontic brackets, dental crowns and the like. The unit can also include elements which provide hand and eye protection. The unit will provide a "dust-free" work area while performing sand blasting and micro-etching. The unit is also inexpensive for a dentist and t is small and portable for easy cleaning of dental appliances."

A specific form of the unit is eight inches tall, six and a half inches wide, and five inches round. It would also have a half of an inch opening on the top, and an inside ledge that would be used to hold a clear plastic lid in place.

Other systems, methods, features, and advantages of the invention will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWING FIGURES

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE INVENTION

Figure 1:
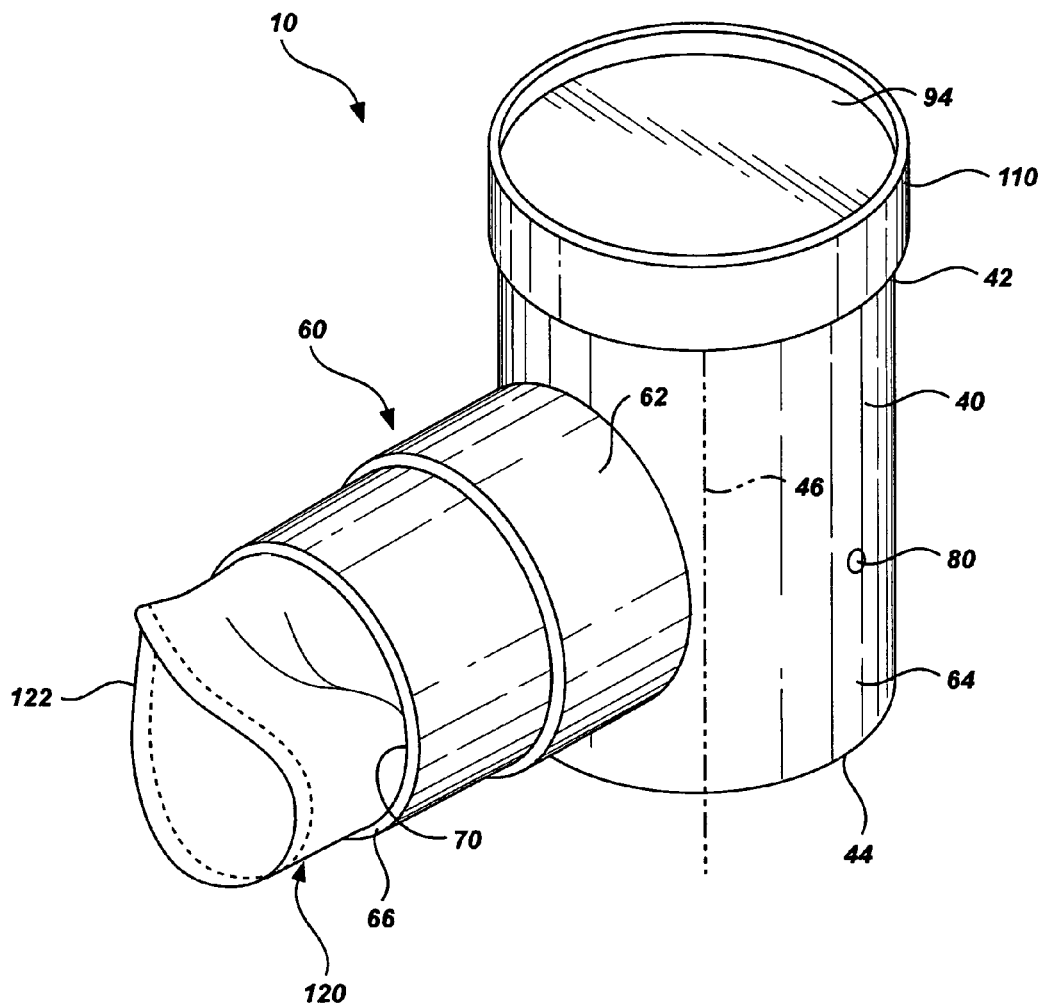
FIG. 1 is a perspective view of a portable unit for containing and controlling debris associated with a dental sanding or micro-etching process for a dental element embodying the principles of the present invention.
Figure 2:
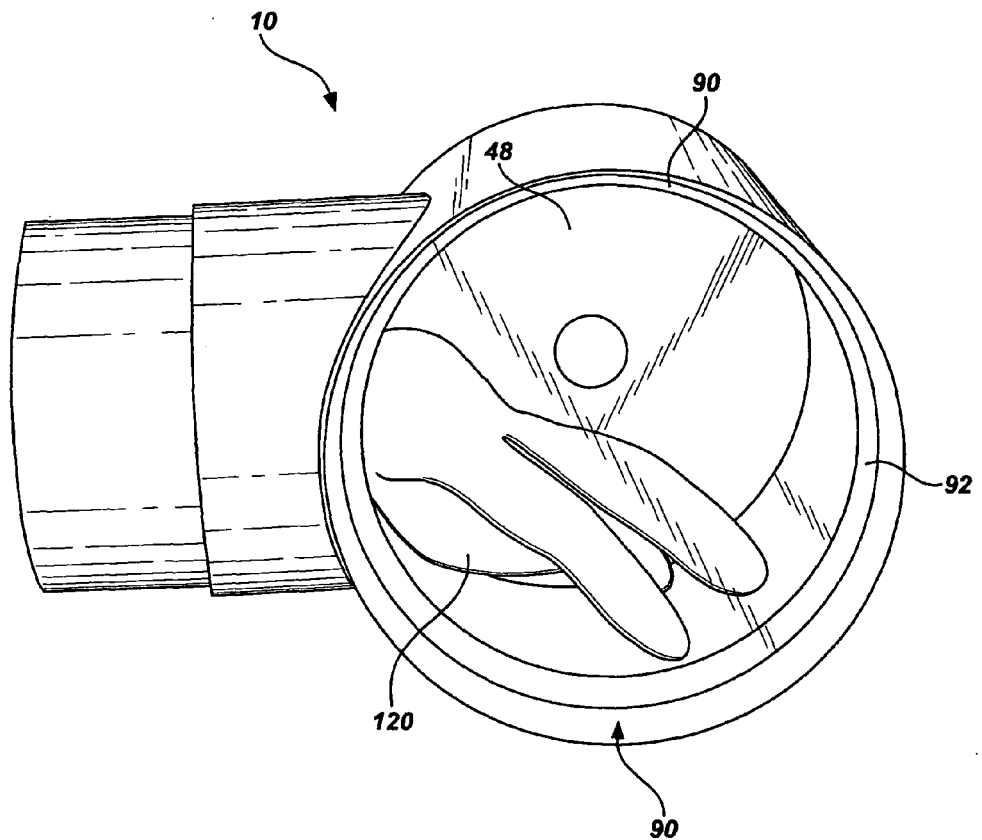
FIG. 2 is a top perspective view of the unit.
Figure 3:
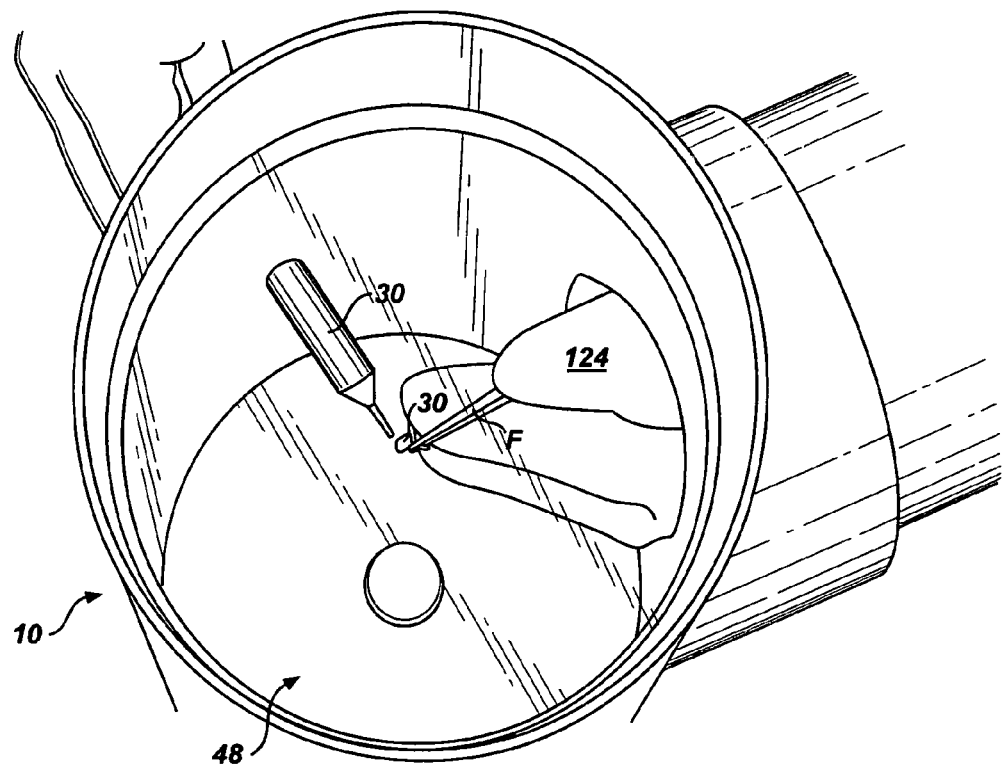
FIG. 3 is a top perspective view of the unit in use.

Referring to the figures, it can be understood that the present invention is embodied in unit 10 for efficiently and economically controlling dust associated with a micro-etching process performed on a dental appliance.

A dental appliance 20, such as a bracket, a crown or the like, to be micro-etched by a micro-etcher 30 which operates on the dental appliance during use in a manner known to those skilled in the art.

The unit includes a first hollow container 40 having a first end 42, a second end 44, a longitudinal axis 46 which extends between the first and second ends of the first container. A bore 48 extends between the first and second ends of the first hollow container. The dental appliance is accommodated in bore 48 of the first container during a micro-etching process.

A second hollow container 60 has a first end 62 unitary with a sidewall 64 of the first container, a second end 66 which is a distal end and which is spaced apart from the first container, and a longitudinal axis 68 which extends between the first and second ends of the second container. A bore 70 is defined through the second container from second end 66 to first end 62 and is connected to the bore of the first container. The second container is oriented with respect to the first container such that the longitudinal axis of the second container is oriented perpendicularly to the longitudinal axis of the first container and the second container is located between the first and second ends of the first container. A user extends his hand through the bore in the second container into the bore of the first container to locate his hand in the bore of the first container to perform the micro-etching process on the dental appliance.

An entry port 80 is defined through sidewall 64 of the first container into bore 48 of the first container and the micro-etcher extends through the entry port into bore 48 of the first container.

A ledge 90 is located on inside surface 92 of the first container adjacent to first end 42 of the first container. A translucent cover 94 is removably mounted on the ledge while end 44 of the first container is closed whereby the first container is closed during a micro-etching process when the cover is in place on the ledge. The translucent cover can be removed to place or retrieve the dental appliance, yet the first container will be closed during the micro-etching process to contain dust and debris associated with that process. A closure ring 110 encircles first end 42 and holds the cover in place on the first container.

A glove 120 is located in the second container and has an entry end 122 located outside the first and second containers with a hand-accommodating portion 124 located in bore 48 of the first container. A user slides his hand into the glove, grasps forceps F or the like to hold the dental appliance during the micro-etching process. It is to be understood that while this disclosure mentions micro-etching, any process associated with work on dental appliances in which debris may result can be carried out in unit 10, and the disclosure of micro-etching is not intended to be limiting. For example, any type of sand blasting operation can be carried out on a dental appliance in unit 10 or the like as will occur to those skilled in the art. Such additional processes are intended to be included in the scope of this disclosure.

In the form shown, the first container is cylindrical and has an axial length of eight inches and a diametric dimension of six and one-half inches and the second container has a diametric dimension of five inches and an axial dimension of four inches so that the unit is portable. The portable nature of unit 10 allows it to be used at several different locations whereby it can be moved from office to office as needed.

While various embodiments of the invention have been described, it will be apparent to those of ordinary skill in the art that many more embodiments and implementations are possible within the scope of this invention. Accordingly, the invention is not to be restricted except in light of the attached claims and their equivalents

What is claimed is:

1. A portable unit for efficiently and economically controlling dust associated with a micro-etching process performed on a dental appliance comprising:
    a first hollow container that is cylindrical and has an axial length of eight inches and a diametric dimension of six and one-half inches in which a dental appliance is accommodated during a micro-etching process;
    a second hollow container having a diametric dimension of five inches and an axial dimension of four inches connected to the first container through which a user places his hand to locate his hand in the first container to perform the micro-etching process on the dental appliance; and
    an entry port on the first container through which a micro-etcher extends into the first container.

2. A unit for efficiently and economically controlling dust associated with a micro-etching process performed on a dental appliance having a bracket comprising:
    a dental appliance to be micro-etched;
    a micro-etcher which operates on the dental appliance during use;
    a first hollow container having a translucent cover supported by a ledge, said first hollow container having a bore including a glove located in the bore to accommodate a user's hand during the micro-etching process, in which bore the dental appliance is accommodated during a micro-etching process;
    a second hollow container including a distal end spaced apart from the first container and a glove extending out of the distal end of the second container connected to the bore of the first container, so configured that the user may extend his hand through the bore in the second container into the bore of the first container to locate his hand in the bore of the first container to perform the micro-etching process on the dental appliance; and
    a port on the first container opening into the bore of the first container through which the micro-etcher extends into the bore of the first container.

* * * * *